United States Patent [19]

Marvin

[11] Patent Number: 5,273,717
[45] Date of Patent: Dec. 28, 1993

[54] SELF-CALIBRATING ANALYZER ASPIRATOR

[75] Inventor: Russel H. Marvin, Webster, N.Y.

[73] Assignee: Eastman Kodak Company, Rochester, N.Y.

[21] Appl. No.: 954,632

[22] Filed: Sep. 30, 1992

[51] Int. Cl.$^5$ .............................. B01L 3/02; G01B 5/14
[52] U.S. Cl. ........................................ 422/100; 422/63; 422/67; 33/561; 33/706; 33/707
[58] Field of Search ........................ 33/561, 706, 707; 250/375, 376; 422/63, 64, 65, 66, 67, 68.1, 100

[56] References Cited

U.S. PATENT DOCUMENTS

| | | | |
|---|---|---|---|
| 4,325,909 | 4/1982 | Coulter et al. | 422/63 |
| 4,519,140 | 5/1985 | Schmitt | 33/706 |
| 4,705,667 | 11/1987 | Marzoner et al. | 422/68 |
| 4,713,974 | 12/1987 | Stone | 73/864.23 |
| 4,716,656 | 1/1988 | Maddock et al. | 33/561 X |
| 4,737,344 | 4/1988 | Koizumi et al. | 422/100 |
| 4,786,803 | 11/1988 | Majette et al. | 356/375 X |
| 4,793,067 | 12/1988 | Reiman et al. | 33/707 |
| 4,824,641 | 4/1989 | Williams | 422/100 |
| 4,844,868 | 7/1989 | Rokugawa | 422/64 |
| 4,854,709 | 8/1989 | Mehnert et al. | 356/375 |
| 5,008,082 | 4/1991 | Shaw | 422/65 |
| 5,052,338 | 10/1991 | Maiorca et al. | 356/375 X |
| 5,115,573 | 5/1992 | Rieder et al. | 33/706 X |
| 5,142,792 | 9/1992 | Nelle | 33/706 X |

Primary Examiner—James C. Housel
Assistant Examiner—Milton I. Cano
Attorney, Agent, or Firm—Dana M. Schmidt

[57] ABSTRACT

A proboscis and method of use that automatically detects whether or not a disposable tip has been properly picked up. The proboscis features a probe supported on a base movable within a driven housing, a sensing flag with multiple signalling stations being fixed to the base. These allow the sensor cooperating with the flag to be fixed to the frame of an analyzer using this proboscis, rather than to be adjustably attached, so that no adjustment is needed of the sensor's position for recalibration.

5 Claims, 5 Drawing Sheets

SELF-CALIBRATING ANALYZER ASPIRATOR

FIELD OF THE INVENTION

The invention relates to a proboscis for use in an analyzer, such as in a dispensing station, with disposable tips.

BACKGROUND OF THE INVENTION

It is conventional, in providing aspirators in an analyzer, to sense the position of the aspirator to prevent vertical overtravel. For example, analyzers provided by Eastman Kodak Company under the trademark "Ektachem 700" have a sensor to determine when the aspirator has lowered a sufficient distance to pick up, by force-fit, a disposable tip. Such sensors are vertically adjusted so that, as part of the set-up calibration, the operator can adjust the trigger location of the sensor depending on that particular analyzer's margins of error. Other instruments have similarly adjusted sensors. See, for example, U.S. Pat. No. 4,705,667 (Column 6, lines 37–44). Once adjusted, the sensor then cooperates with a single flag for each movable part, since that flag is sufficient to trigger that the limiting condition is achieved.

One difficulty of such a construction is that when replacement parts are incorporated into the analyzer proboscis, the set-up calibration (including the positioning of the sensor) has to be recalibrated, which has to be done manually. This is time-consuming and expensive.

Therefore, prior to this invention, there has been a need to provide a proboscis with a sensor for set-up calibration that allows recalibration without readjusting the sensor. This has not been possible with the conventional configuration described above.

Yet another drawback of the previous construction has been that, with only a single flag acting with the sensor, the proboscis can detect only that it has been interrupted. It is unable to determine the nature of the interfering objects since, although the proboscis may be stalled, the flag is not in position to interact with the sensor.

SUMMARY OF THE INVENTION

I have developed an analyzer proboscis and method of detection of tip pickup that solve the above-noted problems.

More specifically, in accord with one aspect of the invention, there is provided a proboscis for aspirating and dispensing liquid in an analyzer, into and out of a disposable tip provided at a tip-pickup station, the proboscis including a probe having a mount surface for releasably supporting a disposable tip, a housing for the probe, a base within the housing supporting the probe within the housing, means for vertically raising and lowering the housing, and sensing means for sensing the vertical position of the probe and comprising a sensor and a flag sensed by the sensor. The proboscis is improved in that the base is movable relative to the housing, the sensor is fixed relative to the analyzer and the flag is fixed with respect to the base and not with respect to the housing, the flag has a plurality of stations detectable by the sensor, and the sensing means further includes means for detecting at what point in the movement of the housing that the flag is no longer moving past the sensor because no more stations are moving past it, so that the distance the probe needs to be lowered to pick up a tip can be readily calibrated.

In accord with another aspect of the invention, there is provided a proboscis for aspirating and dispensing liquid in an analyzer, into and out of a disposable tip provided at a tip-pickup station, the proboscis including a probe having a mount surface for releasably supporting a disposable tip, a housing for the probe, a base movable vertically within the housing and supporting the probe within the housing, means for vertically raising and lowering the housing, and sensing means for sensing the vertical position of the probe, and comprising a sensor and a flag sensed by the sensor. The proboscis is improved in that the probe is movably mounted within the base, and a first compression spring is disposed between the probe and the base, and wherein a second compression spring is disposed between the base and the housing to allow continued movement of said housing after the probe is stalled, to activate the sensing means.

In accord with yet another aspect of the invention, there is provided a process for automatically distinguishing in an analyzer between tip pickup by a proboscis of the analyzer, and no tip pickup, comprising the steps of a) advancing a probe on the proboscis towards a location of tips estimated to be at a specific optimum distance, plus or minus a tolerance factor, by moving a housing towards that location, the probe being movable against a biasing means for biasing the probe out of the housing;

b) detecting cessation of movement of the probe by detecting cessation of movement of a flag fixed to the probe while continuing to move the housing towards the location against the action of the biasing means, c) measuring the distance of movement during step a) until step b) occurs, d) comparing the distance determined in step c) against the optimum distance; and e) determining if the comparison is within the tolerance factor or outside of it to determine that tip pickup has or has not occurred, respectively.

Accordingly, it is an advantageous feature of the invention that an analyzer proboscis and tip pickup process used for aspiration are easily recalibratable when parts are replaced.

Another advantageous feature of this invention is that the structure used to allow recalibration is also effective to automatically detect the proboscis striking objects other than a pipette tip in a tray.

Other advantageous features will become apparent upon reference to the following Description of the Invention when viewed in light of the attached drawings.

DETAILED DESCRIPTION OF THE INVENTION

The invention is hereinafter disclosed in connection with the preferred embodiments, in which the proboscis is used in a particular analyzer, using a particular sensor and a particular drive for the proboscis. In addition, the invention is useful regardless of the construction of the rest of the analyzer, or the type of sensor or drive mechanism used with the proboscis, so long as the proboscis is automatically recalibratable as to the tip pickup station using a sensor fixed in place.

Orientations such as "downwardly", "bottom" and the like refer to orientations existing during the preferred use of the invention.

Figure 1:
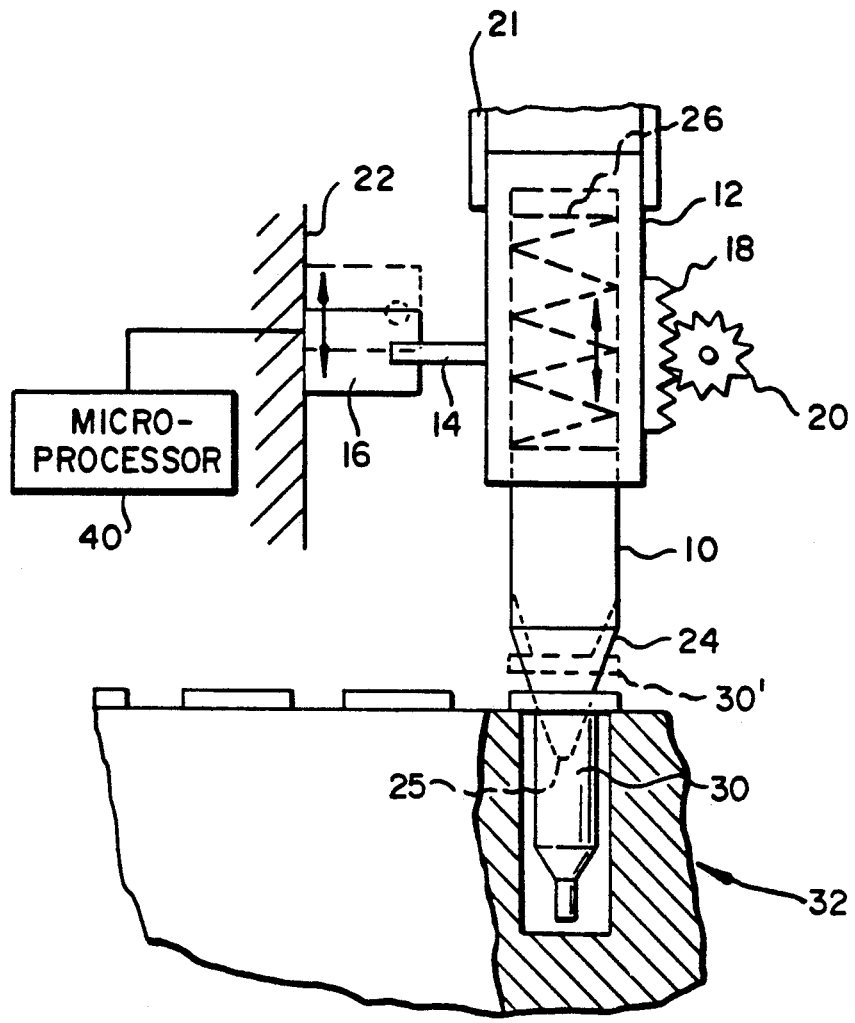
FIG. 1 is a fragmentary elevational view, partially broken away, of a prior art proboscis construction.

The prior art device of FIG. 1 comprises a proboscis featuring a probe 10 mounted within a housing 12 to which is fixed a sensing flag 14 having a single detectable station that cooperates with an adjustable sensor 16, a rack gear 18 providing up and down motion of probe 10 via pinion gear 20. Suitable bearing rail(s) 21 guide the proboscis in its motion. Sensor 16 is mounted on frame 22 of the analyzer and can comprise any electromagnetic radiation emitter and detector. Probe 10 includes a mating surface 24, which can be conical, for seating within and supporting a tip 30 supplied via tray 32. Surface 24 terminates at an end surface 25. (When probe 10 is withdrawn, tip 30 follows it out of tray 32.) Slight vertical compliance is provided between probe 10 and housing 12 by a weak spring 26 compressed within the housing by probe 10. This however is inadequate to allow for substantial changes in vertical location of trays 32 carrying tips 30.

The calibration proceeds as follows: because the position of sensor 16 is adjustable relative to analyzer frame 22, when tray 32 and tip 30 are properly positioned, housing 12 is lowered via gear 20 until tip 30 is seated onto surface 24. Sensor 16 is then adjusted on frame 22 until flag 14 breaks the beam of the sensor, as shown by the solid line positioning of the sensor. Sensor 16 is then temporarily fixed in place. Subsequent breaking of the beam by flag 14 tells microprocessor 40 of the analyzer that tip pickup has occurred.

When recalibration is required due to a change in relative heights, suggested by the phantom position of tip 30', the sensor 16 is released from frame 22 and adjusted to its new position relative to the frame where the flag again is sensed. Such readjustment of sensor 16 requires manual labor.

Figure 2:
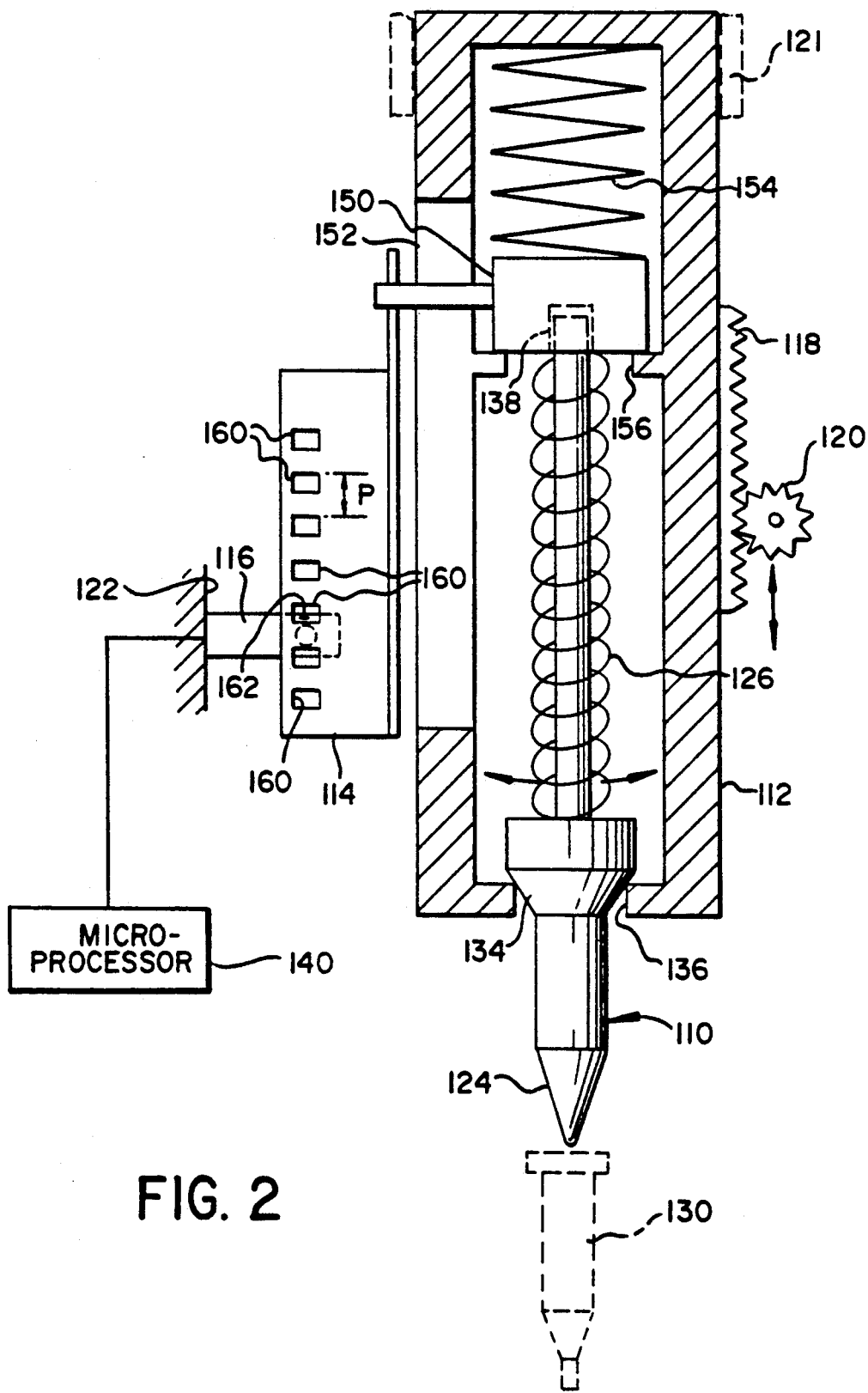
FIG. 2 is a fragmentary elevational section view of a proboscis constructed in accordance with the invention, before contact with a tip.
Figure 3:
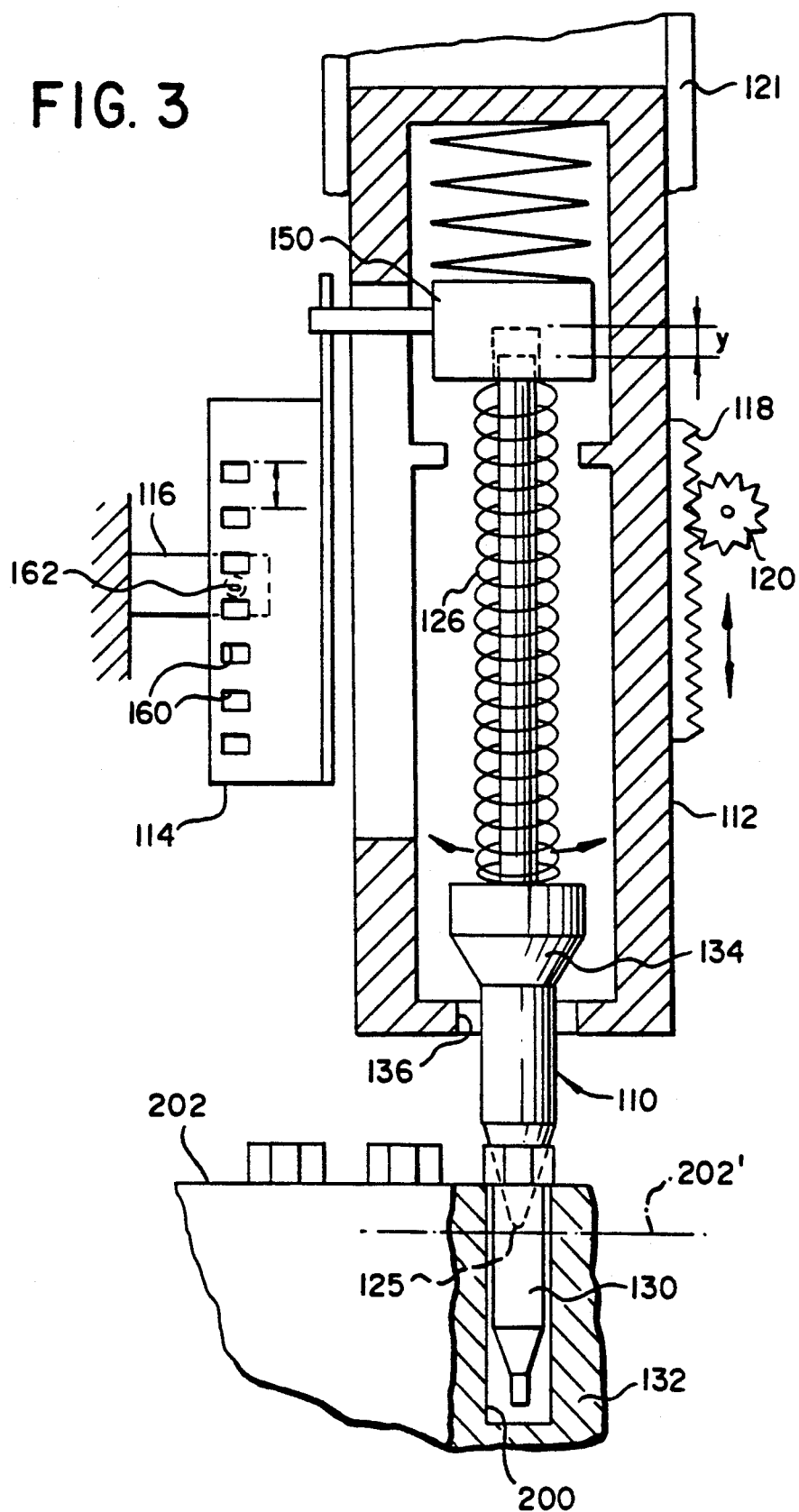
FIG. 3 is a section view similar to that of FIG. 1, but after contact with a tip and after over-driving the housing.

In accordance with the invention, the proboscis is improved as shown in FIGS. 2 and 3. Parts similar to those previously described bear the same reference numeral, to which the distinguishing prefix "1" is applied. Thus, FIG. 2, it comprises a probe 110 movable within a housing 112 driven by a rack gear 118 and driving pinion gear 120, a mating surface 124 being provided to contact, mate, and support a tip 130 on the probe. A flag 114 operatively engages the proboscis in the manner hereinafter described, to cooperate with a sensor 116 on frame 122 of the analyzer. Preferably, sensor 116 comprises an infrared emitter and detector, such as an Optek sensor model OP8981C11. As before, a weak compression spring 126 allows some vertical compliance of probe 110 upon contact between the probe and a tip, or a tip on the probe and a dispensing seat elsewhere in the analyzer.

It is also conventional to provide a self-seating surface 134 on probe 110 for seating within aperture 136 of housing 112, and slight angular freedom at upper end 138 of probe 110 to allow for slight angular adjustment of probe 110 out of the vertical, where necessary.

However, in the invention, probe 110 is carried by a base 150, which in turn is fixed to flag 114, rather than the flag being fixed to the housing 112. A slot 152 is provided in the housing to allow vertical movement of the flag relative to the housing. Further, base 150 is movable within said housing against a relatively strong compression spring 154, a stop member 156 surrounding probe 110 to limit movement of the housing upward relative to base 150 under the expansion of spring 154. Spring 154 preferably provides an expansion force of about 5 kilograms (10 lbs). Still further, flag 114 has a plurality of signalling stations detectable by the sensor, such as cut-outs 160, and sensor 116 is fixed permanently relative to the frame 122 of the analyzer.

Calibration can proceed by an initial machine adjustment that locates beam 162 of the sensor in a "home" position located near the bottom of flag 114. Probe 110 is then stepped down by half-steps, assuming the motor for driving gear 120 (not shown) is a stepper motor, until a good tip pickup is verified by the operator. The number of half-steps needed to do this is stored in a conventional microprocessor 140 as the "optimum" distance for tip pickup. Additionally, a tolerance factor of a certain number of half-steps is stored, this factor being chosen to represent a tip pickup location "close" to optimum. (Microprocessor 140 is preferably programmed in a conventional way.)

Subsequently, the analyzer automatically determines whether good tip pickup occurs, or not, by measuring from the "home" position of probe 110, the number of half-steps before probe 110 stops moving vertically. The cessation of movement of probe 110, FIG. 3, is sensed by reason of the fact that cut-outs 160 stop moving past beam 162, when flag 114 stops due to its attachment to base 150 in which probe 110 is now "bottomed out". However, pinion 120 continues to drive housing 112 downward against spring 154, which downward overdriven movement is used to prevent jarring of the drive connection. A "time-out" cycle is set up in microprocessor 140 such that, when no further flag cut-out 160 is sensed by sensor 114 during the "time-out" period, probe 110 is presumed to be stopped. At this point, pinion gear 120 is also stopped, and sensor 116 and microprocessor 140 combine to generate a signal corresponding to "probe has stopped moving".

Microprocessor 140 has of course counted the half-steps of movement between the "home" position of cut-out 160', FIG. 2, and the stopped position shown in FIG. 3. This is compared, e.g. by subtraction, by microprocessor 140 against the "optimum" number previously determined and stored, and the difference is compared with the "tolerance" factor also stored. (The "tolerance" factor is needed because of the slight vertical variation in tip seating on probe 110 due to variations in, e.g., tip internal diameter tolerances.) If it is outside that factor, a "no tip" error is registered and displayed in the analyzer. For example, the distance moved will be outside that factor if probe 110 moves, in the absence of a tip, all the way into a hole 200 intended to hold a tip in tray 132. It will also be outside that factor if the probe strikes top surface 202 of tray 132, since end surface 125 of mount surface 124 is normally well into the tray for normal tip pickup, as shown. It will also be outside that factor if probe 110 strikes, but does not enter, a tip in the tray.

The distance measured will also be outside the tolerance factor if movement of the probe, and hence flag 114, has ceased because the probe strikes a foreign object. For example, an object sitting on top of tray 132 will cause the probe and flag to cease movement well before the "optimum" distance is reached. The use of multiple cut-outs 160 ensures that this much shorter distance of movement will also be detected using the invention.

Another advantage of the invention is its ease in recalibration in the event of changes to the instrument. For example, replacement of parts can lead to tray 132 having its surface top 202' being located as shown in phantom. In that event, the recalibration occurs by automatic lowering of probe 110 until it makes contact with a tip in a good tip pickup (as visually confirmed by the operator), and storing that new distance moved from the "home" position shown in FIG. 2, as the "optimum" distance. There is thus NO need to manually readjust the physical location of sensor 116 on the frame. Instead, that sensor remains fixed relative to the analyzer.

Figure 4:
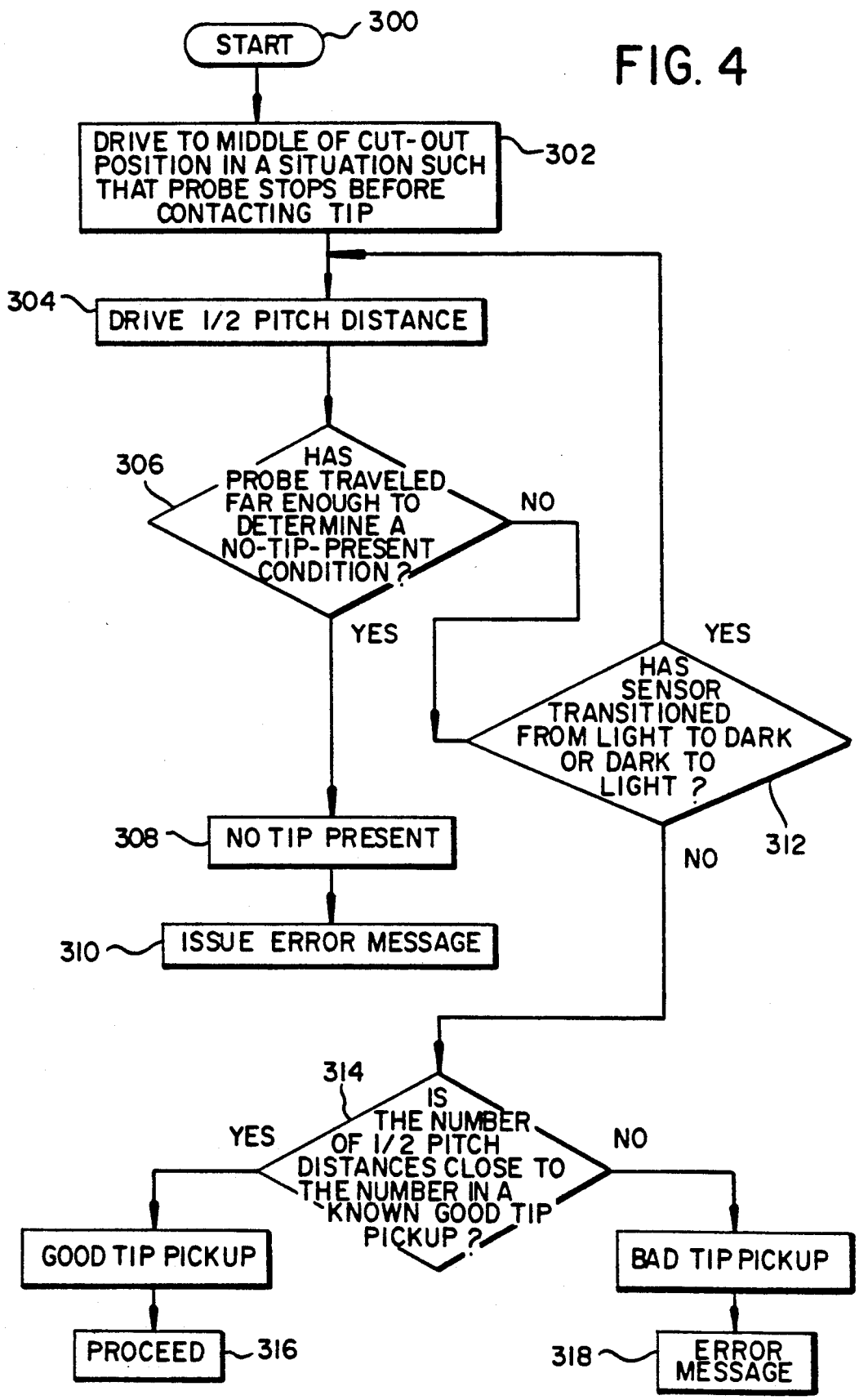
FIGS. 4 and 5 are alternative flow charts useful in programming a computer to provide the process of the invention.
Figure 5:
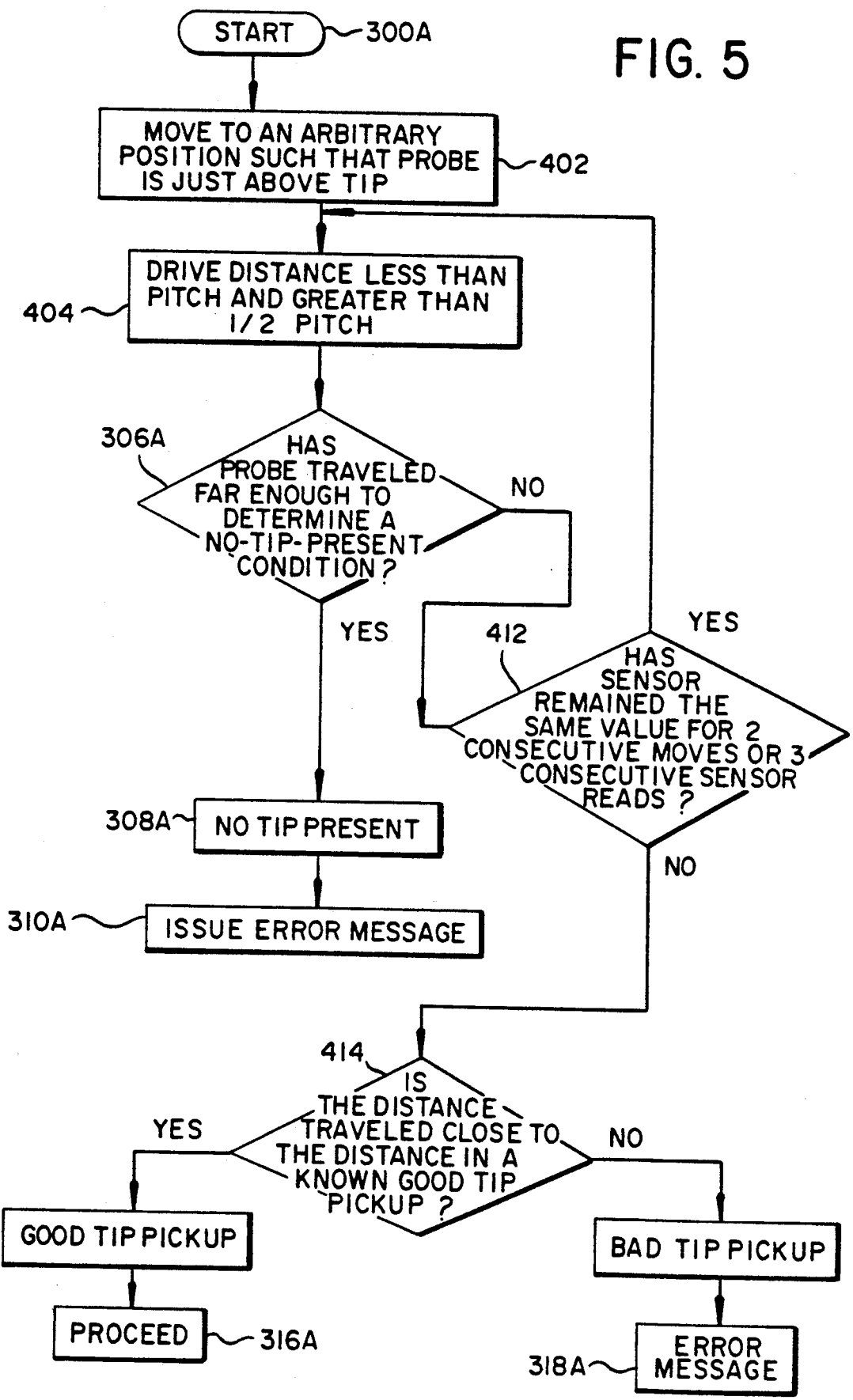

The microprocessor is programmed in a conventional way to carry out the processes described above. The flow charts of FIGS. 4 and 5 are illustrative of the manner in which the programming proceeds: The alternative of FIG. 4 starts the process at step 300. At this point, step 302, drive gear 120 advances housing 112 so that flag 114 arrives with the middle of a cut-out 160 positioned at sensor 116 just before probe 110 enters or touches a tip 130. Step 304, drive gear 120 advances the amount of a half-step of the stepper motor, and the microprocessor queries, step 306, if the advance has achieved the amount that is preset for a "no-tip" condition. If the answer is "yes", condition 308, then an error message of "no tip" is issued, step 310. If the answer is "no", then a second query, step 312, is made as to whether the sensor detected during this step, the passage of cut-outs (transitions from light to dark). If the answer is "yes", then the iterative process is repeated back at step 304. If "no", then a third query, step 314, is made as to whether the ½ pitch distance is within the tolerance distance of the "known good tip pick-up" distance. If "yes", then the analyzer can proceed with subsequent steps, step 316. If "no", then an error message, step 318, is issued that there is an error in the tip pickup.

The alternative flow chart of FIG. 5 incorporates similar features of FIG. 4, and those steps bear the same reference numeral with the distinguishing suffix "A". Steps that are different bear numerals in the 400 series. This alternative differs primarily in that step 402 starts with the probe 110 "just above" contact with a tip, and the drive given to gear 120 is that which produces an advance of flag 114 that is less than pitch "p", FIG. 2, of the cut-outs, but is greater than ½ p. A negative answer to query 306A leads to querying whether sensor 116 has failed to detect a change or not, step 412, for 2 consecutive advances of drive gear 120 or 3 consecutive reads, meaning that in fact the cut-outs are NOT proceeding past the sensor. Then in the case of a negative answer, step 414, the query is whether the distance traveled, whatever it is, is within the tolerance factor of the distance of a known "good" tip pick-up.

As noted, the remaining stations of the analyzer (not shown) can be any convenient construction. Highly preferred is the use of this invention in the dispensing station of the analyzer shown in commonly owned U.S. Pat. No. 5,008,082, the details of which are expressly incorporated herein by reference.

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

What is claimed is:

1. In a proboscis for aspirating and dispensing liquid into and out of a disposable tip provided at a tip-pickup station, said proboscis including a probe having a mount surface for releasably supporting a disposable tip, a housing for said probe, a base within said housing supporting the probe within said housing, means for vertically raising and lowering said housing, and sensing means for sensing the vertical position of said probe and comprising a sensor and a flag sensed by said sensor;
   the improvement wherein said probe, said base, and said housing are each movable relative to the other, a first compression spring being disposed between said probe and said base to push said probe away from said base,
   and wherein a second compression spring is disposed between said base and said housing to allow continued movement of said housing against said second spring after movement of said probe has ceased, to generate a signal with said sensing means,
   said base otherwise being freely movable within said housing, said springs having different spring forces.

2. A proboscis as defined in claim 1, wherein said sensor comprises a single sensing unit having a single electromagnetic radiation emitter and a single detector of said radiation.

3. A proboscis as defined in claim 2, wherein said emitter emits infrared radiation.

4. A proboscis as defined in claim 1, wherein said flag includes means defining a plurality of spaced-apart openings each of which causes said sensor to detect a change in signal.

5. A proboscis as defined in claim 1, wherein said second spring is stronger than said first spring.

* * * * *